United States Patent
Sundermann et al.

(10) Patent No.: US 7,507,758 B2
(45) Date of Patent: Mar. 24, 2009

(54) 4-ALKYL-/4-ALKENYL-/4-ALKYNYL METHYL/-1-ARYL-CYCLOHEXYLAMINE COMPOUNDS

(75) Inventors: Bernd Sundermann, Aachen (DE); Hans Schick, Berlin (DE)

(73) Assignee: Gruenenthal GmbH, Aachen (DE)

( * ) Notice: Subject to any disclaimer, the term of this patent is extended or adjusted under 35 U.S.C. 154(b) by 550 days.

(21) Appl. No.: 11/127,170

(22) Filed: May 12, 2005

(65) Prior Publication Data

US 2005/0267107 A1 Dec. 1, 2005

Related U.S. Application Data

(63) Continuation of application No. PCT/EP03/12314, filed on Nov. 5, 2003.

(30) Foreign Application Priority Data

Nov. 12, 2002 (DE) .................................. 102 52 874

(51) Int. Cl.
A61K 31/405 (2006.01)
C07D 209/04 (2006.01)

(52) U.S. Cl. ..................... 514/415; 548/503; 548/509

(58) Field of Classification Search ................ 548/503, 548/509; 514/415
See application file for complete search history.

(56) References Cited

OTHER PUBLICATIONS

Swahn et al., 1987, CAS: 107:23027.*
J.S. Mogil et al., "Orphanin FQ is a Functional Anti-Opioid Peptide", Neuroscience, 1996, pp. 333-337, vol. 75, No. 2, Elsevier Science Ltd., Great Britain.
Rainer K. Reinscheid et al., "Orphanin FQ: A Neuropeptide That Activates an Opioldlike G Protein-Coupled Receptor," Science, Nov. 3, 1995, pp. 792-794, vol. 270.
Francois Jenck et al., "Orphanin FQ Acts as an Anxiolytic to Attenuate Behavioral Responses to Stress," Proc. Natl. Acad. Sci., Dec. 1997, pp. 14854-14858, vol. 94, USA.
Michael A. King et al., "Spinal Analgesic Activity of Orphanin FQ/Nociceptin and its Fragments", Neuroscience Letters, 1997, pp. 113-116, 223, Elsevier Science Ireland Ltd.

Faud A. Abdulla et al., "Axotomy Reduces the Effect of Analgesic Opioids Yet Increases the Effect of Nociceptin on Dorsal Root Ganglion Neurons," The Journal of Neuroscience, Dec. 1, 1998, pp. 9685-9694, 18, 23, Society for Neuroscience.
Toshiya Manabe et al., "Facilitation of Long-Term Potentiation and Memory in Mice Lacking Nociceptin Receptors", Letters To Nature, Aug. 6, 1998, pp. 577-581, vol. 394, Macmillan Publishers Ltd.
Miyuki Nishi et al., "Unrestrained Nociceptive Response and Dlsregulation of Hearing Ability in Mice Lacking the Nociceptin/OrphaninFQ Receptor," The EMBO Journal, 1997, pp. 1858-1864, vol. 16, No. 8, Oxford University Press.
Girolamo Calo et al., "Pharmacology of Nociceptin and its Receptor: A Novel Therapeutic Target," British Journal of Pharmacology, 2000, pp. 1261-1283, 129, Macmillan Publishers Ltd.
Hiroshi Kawamoto et al., "Synthesis of J-113397, the First Potent and Selective ORL1 Antagonist," Tetrahedron, 2001, pp. 981-986, 57, Elsevier Science Ltd.
Jean-Claude Meunier et al., "Isolation and Structure of the Endogenous Agonist of Opiod Receptor-Like $ORL_1$ Receptor," Letters to Nature, Oct. 12, 1995, pp. 532-535, vol. 377.
William F. Michne et al., "4-(p-Bromophenyl)-4-(dimethylamino)-1-phen-ethylcyclohexanol, and Extremely Potent Representative of a New Analgesic Series", Journal of Medicinal Chemistry, Oct. 1979, pp. 1157-1158, vol. 22, No. 12, American Chemical Society, XP-002216903.
German Search Report dated Aug. 9, 2005.

* cited by examiner

*Primary Examiner*—Rei-tsang Shiao
(74) *Attorney, Agent, or Firm*—Crowell & Moring LLP

(57) ABSTRACT

4-alkyl/4-alkenyl/4-alkynyl methyl/-1-arylcyclohexylamine compounds corresponding to the formula I

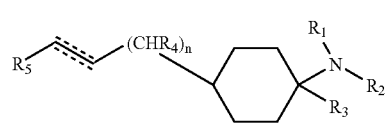

a method for producing them, pharmaceutical compositions containing them, and methods of using them to treat or inhibit pain or other specified conditions associated with the ORL1 receptor.

31 Claims, No Drawings

4-ALKYL-/4-ALKENYL-/4-ALKYNYL METHYL/-1-ARYL-CYCLOHEXYLAMINE COMPOUNDS

CROSS REFERENCE TO RELATED APPLICATIONS

This application is a continuation of international patent application no. PCT/EP2003/012314, filed Nov. 5, 2003, designating the United States of America, and published in German as WO 2004/043900 on May 27, 2004, the entire disclosure of which is incorporated herein by reference. Priority is claimed based on Federal Republic of Germany patent application nos. DE 102 52 874.8 and DE 102 53 322.9, filed Nov. 12, 2002 and Nov. 14, 2002, respectively.

BACKGROUND OF THE INVENTION

The present invention relates to 4-alkyl-/4-alkenyl-/4-alkynylmethyl/-1-aryl-cyclohexylamine compounds, to processes for their preparation, to pharmaceutical compositions containing these compounds and to the use of 4-alkyl-/4-alkenyl-/4-alkynylmethyl/-1-aryl-cyclohexylamine compounds for producing pharmaceutical compositions and for treating or inhibiting pain and other specified conditions involving the ORL1 receptor.

The heptadecapeptide nociceptin is an endogenous ligand of the ORL1 (opioid receptor-like) receptor (Meunier et al, Nature 377, 1995, pp. 532 to 535), which belongs to the opioid receptor family and can be found in many regions of the brain and spinal chord and has a high affinity for the ORL1 receptor. The ORL1 receptor is homologous to the ∥, κ and δ opioid receptors, and the amino acid sequence of the nociceptin peptide has a strong similarity to those of the known opioid peptides. The nociceptin induced activation of the receptor leads, via the coupling with $G_{i/o}$ proteins, to inhibition of adenylate cyclase (Meunier et al, Nature 377, 1995, pp. 532 to 535).

After intracerebroventricular administration, the nociceptin peptide exhibits pronociceptive and hyperalgesic activity in various animal models (Reinscheid et al, Science 270, 1995, pp. 792 to 794). These findings can be described as inhibition of stress-induced analgesia (Mogil et al, Neuroscience 75, 1996, pp. 333 to 337). In this connection, anxiolytic activity of the nociceptin could also be demonstrated (Jenck et al, Proc. Natl. Acad. Sci. USA 94, 1997, 14854 to 14858).

On the other hand, an anti-nociceptive effect of nociceptin could also be demonstrated in various animal models, in particular after intrathecal administration. Nociceptin has an anti-nociceptive effect in various pain models, for example in the tail flick test in mice (King et al, Neurosci. Lett., 223, 1997, 113 to 116). An anti-nociceptive effect of nociceptin, which is of particular interest in that the efficacy of nociceptin increases after axotomy of spinal nerves, could also be demonstrated in models of neuropathic pain. This is in contrast to conventional opioids, of which the efficacy decreases under these conditions (Abdulla and Smith, J. Neurosci., 18, 1998, pp. 9685 to 9684).

The ORL1 receptor is also involved in the regulation of further physiological and pathophysiological processes. These include inter alia learning and memory formation (Manabe et al, Nature, 394, 1997, pp. 577 to 581), Hörvermögen [Hearing capacity] (Nishi et al, EMBO J., 16, 1997, pp. 1858 to 1864) and numerous further processes. In a synopsis by Calo et al (Br. J. Pharmacol., 129, 2000, 1261 to 1283) there is an overview of the indications or biological procedures, in which the ORL1 receptor plays a part or could highly probably play a part. Mentioned inter alia are: analgesia, stimulation and regulation of nutrient absorption, effect on µ-agonists such as morphine, treatment of withdrawal symptoms, reduction of the addiction potential of opioids, anxiolysis, modulation of motor activity, memory disorders, epilepsy; modulation of neurotransmitter release, in particular of glutamate, serotonin and dopamine, and therefore neurodegenerative diseases; influencing the cardiovascular system, triggering an erection, diuresis, anti-natriuresis, electrolyte balance, arterial blood pressure, water-retention disorders, intestinal motility (diarrhoea), relaxation of the respiratory tract, micturation reflex (urinary incontinence). The use of agonists and antagonists such as anoretics, analgesics (also when administered with opioids) or nootropics will also be discussed.

The possibilities for administration of compounds which bind to the ORL1 receptor and activate or inhibit it are correspondingly diverse. In addition thereto, opioid receptors, such as the µ receptor and other sub-types, play an important role in the field of pain therapy but also in the other indications mentioned. It is accordingly advantageous if the compound is also effective with respect to these opioid receptors.

SUMMARY OF THE INVENTION

The object of the present invention was to provide pharmaceutical compositions which act on the nociceptin/ORL1 receptor system and are therefore suitable in particular for pharmaceutical compositions for treating the various diseases associated with this system according to the prior art and are suitable for use in the indications cited therein.

The invention accordingly relates to 4-alkyl-/4-alkenyl-/4-alkynylmethyl/-1-aryl-cyclohexylamine compounds corresponding to formula I

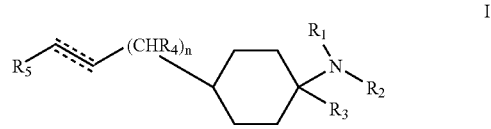

wherein the line illustrated thus:

represents a single, double or triple bond, $R^1$ and $R^2$ independently of one another represent H; respectively saturated or unsaturated, branched or unbranched, singly or multiply substituted or unsubstituted $C_{1-8}$ alkyl or $C_{3-8}$ cycloalkyl; respectively singly or multiply substituted or unsubstituted aryl or heteroaryl; or respectively singly or multiply substituted or unsubstituted aryl, $C_{3-8}$ cycloalkyl or heteroaryl bound by $C_{1-3}$ alkyl, or $R^1$ and $R^2$ together form a ring and represent $CH_2CH_2OCH_2CH_2$, $CH_2CH_2NR^6CH_2CH_2$ or $(CH_2)_{3-6}$, wherein $R^6$ represents H; respectively saturated or unsaturated, branched or unbranched, singly or multiply substituted or unsubstituted $C_{1-8}$ alkyl or $C_{3-8}$ cycloalkyl; respectively singly or multiply substituted or unsubstituted aryl or heteroaryl; or respectively singly or multiply substituted or unsubstituted aryl, $C_{3-8}$ cycloalkyl or heteroaryl bound by $C_{1-3}$ alkyl;

$R^3$ represents respectively saturated or unsaturated, branched or unbranched, singly or multiply substituted or unsubstituted $C_{1-8}$ alkyl or $C_{3-8}$ cycloalkyl; respectively unsubstituted or singly or multiply substituted aryl or heteroaryl; respectively unsubstituted or singly or multiply substituted aryl, $C_{3-8}$ cycloalkyl or heteroaryl bound by a saturated or unsaturated, branched or unbranched, substituted or unsubstituted $C_{1-4}$ alkyl group;

$R^4$ represents H, OH or an O protecting group, wherein n=0 or 1 and an O protecting group denotes, in particular, acetyloxy, benzyloxycarbonyloxy or tert-butoxycarbonyloxy ("OBoc")

$R^5$ represents respectively unsubstituted or singly or multiply substituted $C_{3-8}$ cycloalkyl, aryl or heteroaryl; —$CH_2R^{12}$, —$CH_2$—$CH_2R^{12}$, —$CH_2$—$CH_2$—$CH_2R^{12}$, wherein
  $R^{12}$ represents respectively unsubstituted or singly or multiply substituted $C_{3-8}$ cycloalkyl, aryl or heteroaryl optionally in the form of their racemates, their pure stereoisomers, in particular enantiomers or diastereoisomers or in the form of mixtures of the stereoisomers, in particular the enantiomers or diastereoisomers, in any desired mixing ratio; in the form of their acids or their bases or in the form of their salts, in particular the physiologically acceptable salts or salts of physiologically acceptable acids or cations; or in the form of their solvates, in particular the hydrates.

All of these compounds according to the invention exhibit good binding to the ORL1 receptor, but also to other opioid receptors.

According to this invention, alkyl and cycloalkyl radicals are taken to mean saturated and unsaturated (but not aromatic), branched, unbranched and cyclic hydrocarbons which may be unsubstituted or singly or multiply substituted. In this case, $C_{1-2}$ alkyl represents $C_1$ or $C_2$ alkyl, $C_{1-3}$ alkyl represents $C_1$, $C_2$ or $C_3$ alkyl, $C_{1-4}$ alkyl represents $C_1$, $C_2$, $C_3$ or $C_4$ alkyl, $C_{1-5}$ alkyl represents $C_1$, $C_2$, $C_3$, $C_4$ or $C_5$ alkyl, $C_{1-6}$ alkyl represents $C_1$, $C_2$, $C_3$, $C_4$, $C_5$ or $C_6$ alkyl, $C_{1-7}$ alkyl represents $C_1$, $C_2$, $C_3$, $C_4$, $C_5$, $C_6$ or $C_7$ alkyl, $C_{1-8}$ alkyl represents $C_1$, $C_2$, $C_3$, $C_4$, $C_5$, $C_6$, $C_7$, or $C_8$, $C_{1-10}$ alkyl represents $C_1$, $C_2$, $C_3$, $C_4$, $C_5$, $C_6$, $C_7$, $C_8$, $C_9$ or $C_{10}$ alkyl and $C_{1-8}$ alkyl represents $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$ or $C_{18}$ alkyl. $C_{3-4}$ cycloalkyl also represents $C_3$ or $C_4$ cycloalkyl, $C_{3-5}$ cycloalkyl represents $C_3$, $C_4$ or $C_5$ cycloalkyl, $C_{3-6}$ cycloalkyl represents $C_3$, $C_4$, $C_5$ or $C_6$ cycloalkyl, $C_{3-7}$ cycloalkyl represents $C_3$, $C_4$, $C_5$, $C_6$ or $C_7$ cycloalkyl, $C_{3-8}$ cycloalkyl represents $C_3$, $C_4$, $C_5$, $C_6$, $C_7$ or $C_8$ cycloalkyl, $C_{4-5}$ cycloalkyl represents $C_4$ or $C_5$ cycloalkyl, $C_{4-6}$ cycloalkyl represents $C_4$, $C_5$ or $C_6$ cycloalkyl, $C_{4-7}$ cycloalkyl represents $C_4$, $C_5$, $C_6$ or $C_7$ cycloalkyl, $C_{5-6}$ cycloalkyl represents $C_5$ or $C_6$ cycloalkyl and $C_{5-7}$ cycloalkyl represents $C_5$, $C_6$ or $C_7$ cycloalkyl. With respect to cycloalkyl, the term also includes saturated cycloalkyls, in which one or two carbon atoms are replaced by an S, N or O heteroatom. However, the term "cycloalkyl" also, in particular, includes singly or multiply, preferably singly, unsaturated cycloalkyls without a heteroatom in the ring, provided the cycloalkyl is not an aromatic system, The alkyl and cycloalkyl radicals are preferably methyl, ethyl, vinyl (ethenyl), propyl, allyl (2-propenyl), 1-propynyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, but also adamantyl, $CHF_2$, $CF_3$ or $CH_2OH$ and pyrazolinone, oxopyrazolinone, [1,4]dioxane or dioxolane.

In conjunction with alkyl and cycloalkyl, unless explicitly defined otherwise, the term "substituted", according to this invention, is taken to mean substitution of at least one (or optionally a plurality of) hydrogen radical(s) by F, Cl, Br, I, $NH_2$, SH or OH, wherein the term "multiply substituted" or "substituted" is taken to mean that substitution takes place on different atoms or on the same atoms multiply with the same or different substituents, for example three times on the same C atom, as in the case of $CF_3$ or in various positions, as in the case of —CH(OH)—CH=CH—$CHCl_2$. Particularly preferred substituents in this case are F, Cl and OH. With respect to cycloalkyl, the hydrogen radical can also be substituted by $OC_{1-3}$ alkyl or $C_{1-3}$ alkyl (respectively singly or multiply substituted or unsubstituted), in particular methyl, ethyl, n-propyl, i-propyl, $CF_3$, methoxy or ethoxy.

The term "$(CH_2)_{3-6}$" denotes —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and $CH_2$—$CH_2$—$CH_2$—$CH_2$—$CH_2$—$CH_2$—, $(CH_2)_{1-4}$ is taken to mean —$CH_2$—, —$CH_2$—$CH_2$—, —$CH_2$—$CH_2$—$CH_2$— and —$CH_2$—$CH_2$—$CH_2$—$CH_2$—, $(CH_2)_{4-5}$ is taken to mean —$CH_2$—$CH_2$—$CH_2$—$CH_2$— and —$CH_2$—$CH_2$—$CH_2$—$CH_2$—$CH_2$—, etc.

An aryl radical is taken to mean ring systems comprising at least one aromatic ring, but without heteroatoms in even only one of the rings. Examples include phenyl, naphthyl, fluoranthenyls, fluorenyl, tetralinyl or indanyl, in particular 9H-fluorenyl or anthracenyl radicals, which may be unsubstituted or singly or multiply substituted.

A heteroaryl radical is taken to mean heterocyclic ring systems comprising at least one unsaturated ring, which contains one or more heteroatoms from the group comprising nitrogen, oxygen and/or sulfur and may also be singly or multiply substituted. The following are listed from the group of heteroaryls by way of example: furan, benzofuran, thiophene, benzothiophene, pyrrole, pyridine, pyrimidine, pyrazine, quinoline, isoquinoline, phthalazine, benzo[1,2,5]thiadiazole, benzothiazole, indole, benzotriazole, benzodioxolane, benzodioxane, carbazole, indole and quinazoline.

In conjunction with aryl and heteroaryl, "substituted" is taken to mean substitution of the aryl or heteroaryl by $R^{22}$, $OR^{22}$ a halogen, preferably F and/or Cl, a $CF_3$, a CN, a $NO_2$, a $NR^{23}R^{24}$, a $C_{1-6}$ alkyl (saturated), a $C_{1-6}$ alkoxy, a $C_{3-8}$ cycloalkoxy, a $C_{3-8}$ cycloalkyl or a $C_{2-6}$ alkylene.

In this case, the radical $R^{22}$ represents H, a $C_{1-10}$ alkyl, preferably a $C_{1-6}$ alkyl, an aryl or heteroaryl radical or a saturated or unsaturated aryl or heteroaryl radical bound by $C_{1-3}$ alkyl, wherein these aryl and heteroaryl radicals must not themselves be substituted by aryl or heteroaryl radicals.

The radicals $R^{23}$ and $R^{24}$ are identical or different and represent H, a $C_{1-10}$ alkyl, preferably a $C_{1-6}$ alkyl, an aryl or heteroaryl radical or a saturated or unsaturated aryl or heteroaryl radical bound by $C_{1-3}$ alkyl, wherein these aryl and heteroaryl radicals must not themselves be substituted by aryl or heteroaryl radicals, or the radicals $R^{23}$ and $R^{24}$ together represent $CH_2CH_2OCH_2CH_2$, $CH_2$ $CH_2NR^{25}CH_2CH_2$ or $(CH_2)_{3-6}$.

The radical $R^{25}$ represents H, a $C_{1-10}$ alkyl, preferably a $C_{1-6}$ alkyl, an aryl or heteroaryl radical or a saturated or unsaturated aryl or heteroaryl radical bound by $C_{1-3}$ alkyl, wherein these aryl and heteroaryl radicals must not themselves be substituted by aryl or heteroaryl radicals.

The term "salt" denotes any form of the active ingredient according to the invention in which it assumes or is charged with an ionic form and is coupled to a counter ion (a cation or anion) or is in solution. This also includes complexes of the active ingredient with other molecules and ions, in particular complexes complexed by ionic interactions. In particular this denotes (and this is also a preferred embodiment of this invention) physiologically acceptable salts, in particular physiologically acceptable salts with cations or bases and physiologically acceptable salts with anions or acids or else a salt formed with a physiologically acceptable acid or physiologically acceptable cation.

The term "physiologically acceptable salt with anions or acids" denotes, according to the invention, salts of at least one of the compounds according to this invention—usually protonated, for example on nitrogen—as a cation with at least one anion which are physiologically acceptable—in particular when administered to humans and/or mammals. According to the invention this denotes, in particular, the salt formed with a physiologically acceptable acid, namely salts of the respective active ingredient with inorganic or organic acids which are physiologically acceptable-in particular when administered to humans and/or mammals. Examples of physiologically acceptable salts of specific acids include salts of: hydrochloric acid, hydrobromic acid, sulfuric acid, methane sulfonic acid, formic acid, acetic acid, oxalic acid, succinic acid, malic acid, tartaric acid, mandelic acid, fumaric acid, lactic acid, citric acid, glutamic acid, 1-1-dioxo-1,2-dihydro1b6-benzo[d]isothiazol-3-one (saccharic acid), monomethyl sebacic acid, 5-oxo-proline, hexane-1-sulfonic acid, nicotinic acid, 2-, 3- or 4-amino benzoic acid, 2,4,6-trimethyl-benzoic acid, α-lipoic acid, acetyl glycine, acetylsalicylic acid, hippuric acid and/or aspartic acid. The hydrochloride salt and the citrate salt are particularly preferred.

The term "salt formed with a physiologically acceptable acid", according to this invention, denotes salts of the respective active ingredient with inorganic or organic acids which are physiologically acceptable—in particular when administered to humans and/or mammals. The hydrochloride and the citrate are particularly preferred. Examples of physiologically acceptable acids include: hydrochloric acid, hydrobromic acid, sulfuric acid, methane sulfonic acid, formic acid, acetic acid, oxalic acid, succinic acid, tartaric acid, mandelic acid, fumaric acid, lactic acid, citric acid, glutamic acid, 1,1-dioxo-1,2-dihydro1$\lambda^6$-benzo[d]isothiazol-3-one (saccharic acid), monomethyl sebacic acid, 5-oxo-proline, hexane-1-sulfonic acid, nicotinic acid, 2-, 3- or 4-amino benzoic acid, 2,4,6-trimethyl-benzoic acid, α-lipoic acid, acetyl glycine, acetylsalicylic acid, hippuric acid and/or aspartic acid.

The term "physiologically acceptable salt with cations or bases" denotes, according to the invention, salts of at least one of the compounds according to this invention-usually a (deprotonated) acid-as an anion with at least one, preferably inorganic, cation, which are physiologically acceptable, in particular when administered to humans and/or mammals. The salts of the alkali and alkaline-earth metals are particularly preferred, but also with $NH_4^+$, but in particular (mono-) or (di-) sodium, (mono-) or (di-) potassium, magnesium or calcium salts.

The term "salt formed with a physiologically acceptable cation" denotes, according to the invention, salts of at least one of the respective compounds as an anion with at least one inorganic cation, which are physiologically acceptable, in particular when administered to humans and/or mammals. The salts of the alkali and alkaline-earth metals are particularly preferred, but also $NH_4^+$, but in particular (mono-) or (di-) sodium, (mono-) or (di-) potassium, magnesium or calcium salts.

Preferred according to the invention are 4-alkyl-/4-alkenyl-/4-alkynylmethyl/-1-aryl-cyclohexylamine compounds, wherein $R^1$ and $R^2$ independently of one another represent H; saturated or unsaturated, branched or unbranched, singly or multiply substituted or unsubstituted $C_{1-8}$ alkyl; or $R^1$ and $R^2$ together form a ring and represent $CH_2CH_2OCH_2CH_2$, $CH_2CH_2NR^6CH_2CH_2$ or $(CH_2)_{3-6}$, wherein $R^6$ represents H; saturated or unsaturated, branched or unbranched, singly or multiply substituted or unsubstituted $C_{1-8}$ alkyl.

Preferably, $R^1$ and $R^2$ independently of one another represent H; saturated or unsaturated, branched or unbranched, singly or multiply substituted or unsubstituted $C_{1-4}$ alkyl; wherein $R^1$ and $R^2$ must not both be H, or $R^1$ and $R^2$ together form a ring and represent $(CH_2)_{4-5}$. Particularly preferably, $R^1$ and $R^2$ independently of one another represent methyl or ethyl, or $R^1$ and $R^2$ together form a ring and represent $(CH_2)_5$.

Especially preferred are 4-alkyl-/4-alkenyl-/4-alkynylmethyl/-1-aryl-cyclohexylamine compounds, wherein $R^1$ and $R^2$ independently of one another represent $CH_3$ or H, wherein $R^1$ and $R^2$ do not simultaneously mean H.

Also preferred according to this invention are 4-alkyl-/4-alkenyl-/4-alkynylmethyl/-1-aryl-cyclohexylamine compounds, in which $R^3$ represents respectively unsubstituted or singly or multiply substituted $C_{3-8}$ cycloalkyl, aryl or heteroaryl; respectively unsubstituted or singly or multiply substituted aryl, $C_{3-8}$ cycloalkyl or heteroaryl bound by a saturated or unsaturated, unbranched, substituted or unsubstituted $C_{1-2}$ alkyl group. Preferably, $R^3$ represents respectively unsubstituted or singly or multiply substituted cyclopentyl, cyclohexyl, phenyl, benzyl, naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl; respectively unsubstituted or singly or multiply substituted $C_{5-6}$ cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bound by a saturated, unbranched $C_{1-2}$ alkyl group. It is particularly preferred if $R^3$ represents respectively unsubstituted or singly or multiply substituted phenyl, furyl, thiophenyl, naphthyl, benzyl, benzofuranyl, indolyl, indanyl, benzodioxanyl, benzodioxolanyl, pyridyl, pyrimidyl, pyrazinyl or benzothiophenyl; respectively unsubstituted or singly or multiply substituted phenyl, furyl or thiophenyl bound by a saturated, unbranched $C_{1-2}$ alkyl group.

Especially preferred are 4-alkyl-/4-alkenyl-/4-alkynylmethyl/-1-aryl-cyclohexylamine compounds, in which $R^3$ represents respectively substituted or unsubstituted phenyl, thiophenyl, pyridyl or benzyl, particularly preferably phenyl.

Also preferred are 4-alkyl-/4-alkenyl-/4-alkynylmethyl/-1-aryl-cyclohexylamine compounds in which $R^5$ represents respectively unsubstituted or singly or multiply substituted $C_{3-8}$ cycloalkyl, aryl or heteroaryl. Preferably, $R^5$ represents respectively unsubstituted or singly or multiply substituted cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl. Most particularly preferably, $R^5$ represents respectively unsubstituted or singly or multiply substituted cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl.

Also preferred are 4-alkyl-/4-alkenyl-/4-alkynylmethyl/-1-aryl-cyclohexylamine compounds, in which $R^5$ represents —$CH_2R^{12}$, —$CH_2$—$CH_2R^{12}$, —$CH_2$—$CH_2$—$CH_2R^{12}$. Preferably, $R^5$ represents —$CH_2R^{12}$, —$CH_2$—$CH_2R^{12}$. Particularly preferably, $R^5$ represents —$CH_2R^{12}$.

$R^{12}$ in the foregoing groups represents respectively unsubstituted or singly or multiply substituted $C_{3-8}$ cycloalkyl, aryl or heteroaryl. Preferably, $R^{12}$ represents respectively unsubstituted or singly or multiply substituted cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl. It is particularly preferred if $R^{12}$ represents respectively unsubstituted or singly or multiply substituted cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl.

Most particularly preferred are 4-alkyl-/4-alkenyl-/4-alkynylmethyl/-1-aryl-cyclohexylamine compounds selected from the group consisting of:
dimethyl-[1-phenyl-4-(2-p-tolylvinyl)cyclohexyl]amine hydrochloride, most polar diastereoisomer;
dimethyl-[1-phenyl-4-(2-p-tolylvinyl)cyclohexyl]amine hydrochloride, second most polar diastereoisomer;
dimethyl-[1-phenyl-4-(2-p-tolylvinyl)cyclohexyl]amine hydrochloride, least polar diastereoisomer;
{4-[2-(4-fluorophenyl)vinyl]-1-phenylcyclohexyl}dimethylamine hydrochloride, least polar diastereoisomer;
{4-[2-(4-fluorophenyl)vinyl]-1-phenylcyclohexyl}dimethylamine hydrochloride, second least polar diastereoisomer;
{4-[2-(4-fluorophenyl)vinyl]-1-phenylcyclohexyl}dimethylamine hydrochloride, second most polar diastereoisomer;
{4-[2-(4-fluorophenyl)vinyl]-1-phenylcyclohexyl}dimethylamine hydrochloride, most polar diastereoisomer;
{4-[3-(1H-indol-3-yl)-propenyl]-1-phenylcyclohexyl}dimethylamine hydrochloride, more polar diastereoisomer;
{4-[3-(1H-indol-3-yl)-propenyl]-1-phenylcyclohexyl}dimethylamine hydrochloride, less polar diastereoisomer;
3-[3-tert-butoxycarbonyloxy-3-(4-dimethylamino-4-phenyl-cyclohexyl)-prop-1-ynyl]indol-1-carboxylic acid-tert-butylester, less polar diastereoisomer;
3-[3-tert-butoxycarbonyloxy-3-(4-dimethylamino-4-phenyl-cyclohexyl)-prop-1-ynyl]indol-1-carboxylic acid-tert-butylester, more polar diastereoisomer;
3-[3-(4-dimethylamino4-phenyl-cyclohexyl)-3-hydroxyprop-1-ynyl]-indol-1-carboxylic acid-tert-butylester;
and mixtures of two or more of the foregoing.

The substances according to the invention act, for example, on the ORL1 receptor that is relevant in connection with various diseases as well the μ-opiate receptor, so they are suitable as a pharmaceutical active ingredient in a pharmaceutical composition. The invention accordingly also relates to pharmaceutical compositions containing at least one 4-alkyl-/4-alkenyl-/4-alkynylmethyl/-1-aryl-cyclohexylamine compound. In addition to the at least one 4-alkyl-/4-alkenyl-/4-alkynylmethyl/-1-aryl-cyclohexylamine compound according to the invention, the pharmaceutical compositions according to the invention may also contain suitable additives and/or auxiliaries as well as excipients, fillers, solvents, diluents, dyes and/or binders.

The pharmaceutical compositions of the invention can be administered as liquid pharmaceutical preparations in the form of injection solutions, drops or juices, as semi-solid pharmaceutical preparations in the form of granules, tablets, pellets, patches, capsules, plasters or aerosols. The choice of auxiliaries, etc. and the amounts thereof to be used depend on whether the pharmaceutical composition is to be administered orally, perorally, parenterally, intravenously, intraperitoneally, intradermally, intramuscularly, intranasally, buccally, rectally or topically, for example to the skin, the mucous membranes or the eyes. Preparations in the form of tablets, dragees, capsules, granules, drops, juices and syrups are suitable for oral administration; solutions, suspensions, easily reconstitutable dry preparations and sprays are suitable for parenteral, topical and inhalative administration. 4-alkyl-/4-alkenyl-/4-alkynylmethyl/-1-aryl-cyclohexylamine compounds according to the invention in a deposit, in dissolved form or in a plaster, optionally with the addition of agents to promote skin penetration, are preparations suitable for percutaneous administration. Orally or percutaneously administrable forms of preparation can release the 4-alkyl-/4-alkenyl-/4-alkynylmethyl/-1-aryl-cyclohexylamine compound according to the invention after a delay. In principle, further active ingredients known to the person skilled in the art can be added to the pharmaceutical compositions according to the invention.

The amount of active ingredient to be administered to the patient varies as a function of the weight of the patient, the method of administration, the indication and the severity of the disease. Typically, 0.005 to 1,000 mg/kg, preferably 0.05 to 5 mg/kg, of at least one 4-alkyl-/4-alkenyl-/4-alkynylmethyl/-1-aryl-cyclohexylamine compound according to the invention are administered.

For all of the above-mentioned forms of the pharmaceutical compositions according to the invention, it is particularly preferred if, in addition to at least one 4-alkyl-/4-alkenyl-/4-alkynylmethyl/-1-aryl-cyclohexylamine compound, the pharmaceutical composition contains a further active ingredient, in particular an opioid, preferably a strong opioid, in particular morphine, or an anaesthetic, preferably hexobarbital or halothane.

In one preferred form of the pharmaceutical composition, a contained 4-alkyl-/4-alkenyl-/4-alkynylmethyl/-1-aryl-cyclohexylamine compound according to the invention is in the form of a pure diastereoisomer and/or enantiomer, a racemate or a non-equimolar or equimolar mixture of the diastereoisomers and/or enantiomers.

As stated above in discussing the background of the invention, the ORL1 receptor has been identified in particular in the phenomenon of pain. Accordingly, 4-alkyl-/4-alkenyl-/4-alkynylmethyl/-1-aryl-cyclohexylamine compounds according to the invention may be used for producing a pharmaceutical composition for the treatment of pain, in particular acute, neuropathic or chronic pain. The invention accordingly also relates to the use of a 4-alkyl-/4-alkenyl-/4-alkynylmethyl/-1-aryl-cyclohexylamine compound according to the invention for producing a pharmaceutical composition for the treatment of pain, in particular acute, visceral, neuropathic or chronic pain.

The invention also relates to the use of a 4-alkyl-/4-alkenyl-/4-alkynylmethyl/-1-aryl-cyclohexylamine compound according to the invention for producing a pharmaceutical composition for the treatment of anxiety, stress and stress-related syndromes, depression, epilepsy, Alzheimer's disease, senile dementia, general cognitive dysfunction, learning and memory disorders (as a nootropic), withdrawal symptoms, alcohol and/or drug and/or medicine abuse and/or dependency, sexual dysfunction, cardiovascular diseases, hypotension, hypertension, tinnitus, pruritus, migraine, hearing difficulties, deficient intestinal motility, impaired nutrient absorption, anorexia, obesity, locomotive disorders, diarrhoea, cachexia, urinary incontinence, or as a muscle relaxant, anti-convulsive or anaesthetic or for co-administration in treatment with an opioid analgesic or anaesthetic, for diuresis or anti-natriuresis, anxiolysis, for modulation of motor activity, for modulation of neurotransmitter release and treatment of neurodegenerative diseases associated therewith, for the treatment of withdrawal symptoms and/or for reducing opioid addiction potential.

In some of the above uses it may be preferred if a 4-alkyl-/4-alkenyl-/4-alkynylmethyl/-1-aryl-cyclohexylamine compound that is used is in the form of a pure diastereoisomer and/or enantiomer, a racemate or a non-equimolar or equimolar mixture of the diastereoisomers and/or enantiomers.

The invention also relates to a method for the treatment, in particular in one of the above-mentioned indications, of a non-human mammal or of a human, which or who requires treatment of pain, in particular chronic pain, by administration of a therapeutically effective dose of a 4-alkyl-/4-alkenyl-/4-alkynylmethyl/-1-aryl-cyclohexylamine compound according to the invention, or of a pharmaceutical composition according to the invention.

The invention also relates to a method for producing the 4-alkyl-/4-alkenyl-/4-alkynylmethyl/-1-aryl-cyclohexylamine compound according to the invention as set forth in the following description and examples. In this regard, the following main method is particularly suitable for producing a 4-alkyl-/4-alkenyl-/4-alkynylmethyl/-1-aryl-cyclohexylamine compound according to the invention in which $R^1$, $R^2$, $R^3$, $R^4$ and $R^5$ have the meanings given for compounds of the invention according to formula I, and $R^{01}$ and $R^{02}$ independently of one another represent a protecting group or have the meanings given for $R^1$ and $R^2$ in compounds according to the invention of formula I. This main method comprises the following steps:

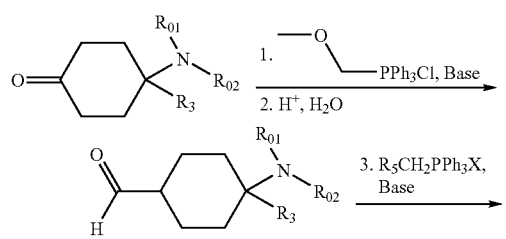

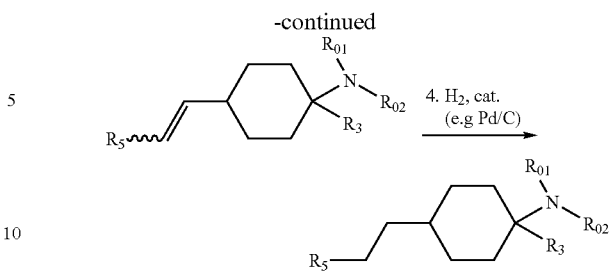

In a first step, 4-aminocyclohexanone compounds are reacted with methoxytriphosphonium chloride and a base, for example sodium hydride, and subsequently with aqueous acid, e.g., HCl, to form corresponding aldehydes.

In the second step the 4-aminocyclohexane carbaldehyde compounds obtained in the first step are reacted with Wittig reagents corresponding to formula $R^5CH_2PPh_3X$ in the presence of base, and the resulting olefins are optionally reduced to the alkane, for example catalytically with $H_2$, for example using Pd/C.

Alternative General Synthesis Pattern

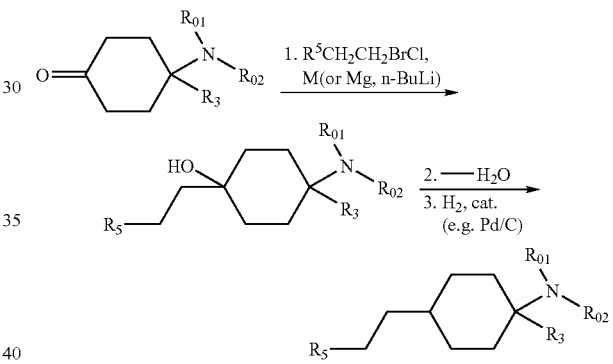

Alternatively, 4-alkyl-/4-alkenyl/4-alkynyl methyl/-1-aryl-cyclohexylamine compounds may also be produced by reacting 4-aminocyclohexanones with an organometallic compound, which may be produced from $R^5CH_2CH_2Br$ or $R^5CH_2CH_2Cl$ with the addition of a suitable metal or a suitable organometallic compound, for example magnesium or n-BuLi, and be subsequently dehydrated by addition of acid and catalytically hydrogenated with $H_2$, for example using Pd/C.

Synthesis Scheme for Alkyne Compounds and Alkyl-Substituted Compounds

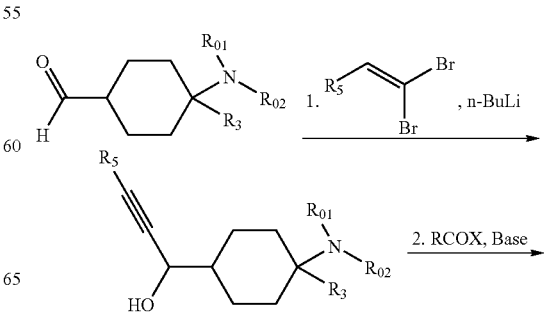

-continued

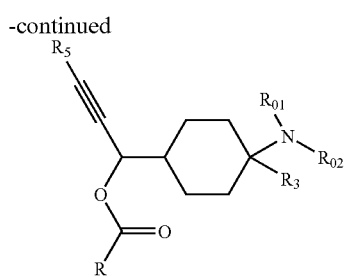

When producing alkyne compounds and compounds substituted on the alkyl chain, 4-amino-cyclohexyl carbaldehydes are reacted with

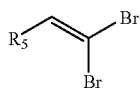

in the presence of n-BuLi to form 4-alkynylmethyl-cyclohexylamine compounds according to the invention, wherein $R^4$ represents OH. By protecting the OH function using a protecting group and subsequent hydrogenation of the triple bond, for example with $H_2$/Pd or $H_2$ using $Pd/C+BaSO_4$ (Lindlar catalyst), the corresponding alkyl and alkene compounds are obtained.

The preparation of suitable 4-aminocyclohexanones is known from the literature (Lednicer et al, J. Med. Chem., 23, 1980, 424-430; WO 0290317).

Isolation of the compounds according to the invention by column chromatography using silica gel as the stationary phase and ethyl acetate, methanol, from ethyl acetate and methanol or mixtures of ethyl acetate and diethyl ether as the eluant leads to separation of the diastereoisomers of different polarity. These were characterised on the basis of their run time during separation as "least polar diastereoisomer" (shortest run time) to "most polar diastereoisomer" (longest run time).

EXAMPLES

The following examples will serve to illustrate the invention in further detail without, however, limiting the scope of the invention. The yields of the compounds produced are not optimized. All temperatures are uncorrected.

The term "ether" means diethyl ether, "EE" ethyl acetate and "DCM" dichloromethane, "DMF" dimethyl formamide, "DMSO" dimethyl sulfoxide and "THF" tetrahydrofuran. The term "equivalents" means amount of substance equivalents, "mp." melting point or melting range, "decomp." decomposition, "RT" room temperature, "abs." absolute (anhydrous), "rac." racemic, "conc." concentrated, "min" minutes, "h" hours, "d" days, "vol. %" volume percent, "m %" mass percent and "M" is an indication of concentration in mol/l.

Silica gel 60 (0.040 to 0.063 mm) from E. Merck, Darmstadt was used as the stationary phase for column chromatography. The thin-layer chromatography tests were carried out using HPTLC chromatoplates, silica gel 60 F 254, from E. Merck, Darmstadt. The mixing ratios of eluants for chromatography tests are always given in volume/volume.

Example 1

Dimethyl-[1-phenyl-4-(2-p-tolylvinyl)cyclohexyl] amine hydrochloride, most polar diastereoisomer Methoxymethyltriphenylphosphonium chloride (6.3 g, 18.4 mmole) was dissolved in DMF (25 ml) under argon and sodium hydride was added (60% in mineral oil, 737 mg, 18.4 mmole). 4-dimethylamino-4-phenylcycohexanone (2.0 g, 9.2 mmole), dissolved in 25 ml DMF, was added dropwise over 30 min and the suspension stirred for 3 d at RT. For working up, the suspension was slowly poured into a 2M HCl (50 ml) cooled with chilled water, stirred for 2 h at RT and subsequently extracted with diethyl ether (5×25 ml) and EE (6×20 ml). The aqueous phase was then brought to pH 10 to 11 using 1M NaOH and extracted using EE (5×20 ml). The combined extracts were dried with sodium sulfate, filtered and evaporated. The residue was 4-dimethylamino-4-phenylcycohexane carbaldehyde (2.0 g brown oil) in the diastereoisomer ratio 55:45 ($^1$H-NMR).

4-methylbenzyltriphenyl phosphonium chloride (1.61 g, 4 mmole) was suspended under argon in abs. DMF, cooled to 0° C., sodium hydride (200 mg, 60% in mineral oil, 5 mmole) was added in portions and the mixture stirred for 30 min. 4-dimethylamino-4-phenylcycohexane carbaldehyde (463 mg, 2 mmole) was dissolved in DMF and added dropwise within 35 min. After slow heating to RT the mixture was stirred for 2 d. For working up, DMF was distilled off to about 4 ml, the residue was cooled to 0° C. and 15 ml 2N HCl added while stirring. The aqueous suspension was extracted with ether (5×20 ml) and the combined extracts dried, filtered and evaporated, 1.85 g crude product being obtained as a tacky beige solid. The aqueous phase was brought to pH 10 with 1M NaOH and extracted with EE (3×15 ml). The combined extracts were dried, filtered and evaporated, wherein a further 113 mg crude product were obtained. The combined crude products were purified by flash chromatography on silica gel (170 g, eluant: 2,500 ml EE/MeOH (3:1)]. 120 mg of the most polar diastereoisomer of dimethyl-[1-phenyl-4-(2-p-tolylvinyl)cyclohexyl]amine were obtained (mp. 130 to 145° C.), of which 110 mg (0.34 mmole) were dissolved in 2-butanone/acetone (4 ml/2 ml) in heat. Chlorotrimethyl silane (131 µl, 1 mmole) was added dropwise at RT and stirred for 3 h. The solvent was completely distilled off, the residue covered with abs. ether and mechanically detached from the flask wall. The hygroscopic solid thus obtained was dried under vacuum. The hydrochloride of the diastereoisomer of dimethyl-[1-phenyl-4-(2-p-tolylvinyl)cyclohexyl]amine was thus obtained in a yield of 122 mg (beige hygroscopic solid, mp. 140 to 150° C.).

Example 2

Dimethyl-[1-phenyl-4-(2-p-tolylvinyl)cyclohexyl] amine hydrochloride, second most polar diastereoisomer As described for Example 1, 84 mg of the second most polar diastereoisomer were also obtained (mp. 108 to 120° C.), of which 80 mg (0.25 mmole) were dissolved in heat in 2-butanone/methanol (5 ml/3 ml), ethanolic 3.3M HCl (228 µl, 0.8 mmole) was added at RT and the mixture stirred for 60 min. The mixture was evaporated to dryness, the residue covered with ether and mechanically detached from the flask wall. The solid was suction filtered and washed with ether (2×2 ml). The hydrochloride of the second most polar diastereoisomer of dimethyl-[1-phenyl-4-(2-p-tolylvinyl)cyclohexyl]amine was thus obtained in a yield of 87 mg (beige solid, mp. 155 to 163° C.).

Example 3

Dimethyl-[1-phenyl-4-(2-p-tolylvinyl)cyclohexyl] amine hydrochloride, least polar diastereoisomer As described for Example 1, 57 mg of the least polar diastereoisomer were also obtained (mp. 165 to 170° C.), of which 50 mg (0.16 mmole) were dissolved in acetone/2-butanone/methanol (20 ml/10 ml/10 ml) in heat, ethanolic 3.3M HCl (142 μl, 0.5 mmole) was added at RT and the mixture stirred for 60 min. The mixture was evaporated to dryness, the residue covered with ether and mechanically detached from the flask wall. The ether was decanted off and the residue dried under vacuum. The hydrochloride of the least polar diastereoisomer dimethyl-[1-phenyl-4-(2-p-tolylvinyl)cyclohexyl]amine was thus obtained in a yield of 51 mg (beige solid, mp. 208 to 212° C.).

Example 4

{4-[2-(4-fluorophenyl)vinyl]-1-phenylcyclohexyl}dimethylamine hydrochloride, least polar diastereoisomer 4-fluorobenzyltriphenyl phosphonium chloride (1.22 g, 3 mmole) was suspended under argon in abs. THF (15 ml) and cooled to −5° C. Potassium-tert-butanolate (337 mg, 3 mmole) dissolved in THF (14 ml) was added dropwise and the mixture post-stirred for 30 min at <0°. 4-dimethylamino-4-phenylcyclohexane carbaldehyde (467 mg, 2 mmole) dissolved in THF (8 ml) was subsequently added dropwise and the mixture stirred for 20 h with gradual heating to RT. For working up, the mixture was evaporated and 15 ml 1M HCl, 5 ml water and 30 ml ether were added to the residue. After stirring for 60 min, between the aqueous phase and the organic phase, there was a white solid which was suction filtered and washed with ether (3×2 ml). Following analysis and DC, this solid was the hydrochloride of the least polar of four possible diastereoisomers of {4-[2-(4-fluorophenyl)vinyl]-1-phenylcyclohexyl}dimethylamine (145 mg, mp. 255 to 258° C.).

Example 5

{4-[2-(4-fluorophenyl)vinyl]-1-phenylcyclohexyl}dimethylamine hydrochloride, second least polar diastereoisomer The clear phases of the filtrate obtained according to Example 4 were separated, the aqueous phases washed with diethyl ether (5×20 ml), adjusted to pH 10 with 1N NaOH and extracted with EE (4×20 ml). The combined extracts were dried, filtered and evaporated. The residue (357 mg dark brown oil) contained the three further diastereoisomers of {4-[2-(4-fluorophenyl)vinyl]-1-phenylcyclohexyl}dimethylamine. Separation of the diastereoisomers was achieved by flash chromatography on silica gel [35 g, eluant: 350 ml EE/MeOH (5:1); 300 ml EE/MeOH (4:1); 300 ml EE/MeOH (1:1)]. 66 mg of the second least polar diastereoisomer were obtained which were dissolved in 2-butanone (1.5 ml), and subsequently 3.3M ethanolic HCl (185 μl, 0.61 mmole) was added and the mixture stirred for 2 h. The mixture was evaporated to dryness and the residue taken up in two drops of MeOH, and subsequently ether (4 ml) was added. The resultant solid was suction filtered and washed with ether (1×1 ml). The hydrochloride of the second least polar diastereoisomer of {4-[2-(4-fluorophenyl)vinyl]-1-phenylcyclohexyl}dimethylamine was thus obtained as a white solid (60.0 mg, mp. 159 to 167° C.).

Example 6

{4-[2-(4-fluorophenyl)vinyl]-1-phenylcyclohexyl}dimethylamine hydrochloride, second most polar diastereoisomer As described for Example 5, 69 mg of the second most polar diastereoisomer of {4-[2-(4-fluorophenyl)vinyl]-1-phenylcyclohexyl}dimethylamine were also obtained (yellow oil) which were dissolved in 2-butanone (1.5 ml), and subsequently 3.3M ethanolic HCl (194 μl, 0.6 mmole) was added and the mixture stirred for 2 h. After evaporating to dryness the residue was dissolved in two drops of MeOH, and subsequently ether (8 ml) was added. The resultant residue was suction filtered and washed with ether (2×1 ml). The hydrochloride of the second most polar diastereoisomer of {4-[2-(4-fluorophenyl)vinyl]-1-phenylcyclohexyl)dimethylamine was thus obtained as a white solid (70 mg, mp 177 to 188° C.).

Example 7

{4-[2-(4-fluorophenyl)vinyl]-1-phenylcyclohexyl}dimethylamine hydrochloride, most polar diastereoisomer As described for Example 5, 132 mg of the most polar diastereoisomer of 4-[2-(4-fluorophenyl)vinyl]-1-phenylcyclohexyl)dimethylamine were also obtained which were dissolved in 2-butanone/ethanol (2 ml/10 ml) in heat, and subsequently 3.3M ethanolic HCl (371 μl, 1.2 mmole) was added and the mixture stirred for 60 min. After evaporating to dryness the residue was covered in ether (2 ml) and mechanically separated from the flask wall. The solid was suction filtered and washed with ether (2×0.5 ml). The hydrochloride of the most polar diastereoisomer of {4-[2-(4-fluorophenyl)vinyl]-1-phenylcyclohexyl}dimethylamine was thus obtained as a white solid (126 mg, mp with disintegration above about 140° C.).

Example 8

{4-[3-(1H-indol-3-yl)-propenyl]-1-phenylcyclohexyl}dimethylamine hydrochloride, polar diastereoisomer

[2-(1H-indol-3-yl)ethyl]triphenyl phosphonium bromide (1.94 g, 4 mmole) was suspended under argon in abs. THF (15 ml) and cooled to −5° C. Potassium-tert-butanolate (448.9 mg, 4 mmole) dissolved in THF (15 ml) was added dropwise and the mixture stirred for 30 min at 0° C. 4-dimethylamino-4-phenylcyclohexane carbaldehyde (463 mg, 2 mmole) dissolved in THF (7 ml) was added dropwise within 40 min. The mixture was stirred for 2 d with gradual heating to RT. For working up, the THF was distilled off and 1M HCl (20 ml), water (5 ml) and ether (30 ml) were added to the residue. After stirring for one hour there was a viscous brown layer between the aqueous phase and the organic phase. The organic phase was separated, the aqueous phase and the viscous layer were vigorously shaken with dichloromethane (3×5 ml). The clear phases were separated, the combined dichloromethane extracts were washed with 5% NaHCO₃ solution (15 ml), dried, filtered and evaporated. The crude product obtained was purified by flash chromatography on silica gel [130 g eluant; 600 ml EE/MeOH (15:1); 700 ml EE/MeOH (10:1); 1,500 ml EE/MeOH (5:1); 700 ml MeOH]. A polar diastereoisomer of the four possible diastereoisomers was thus isolated in pure form (62 mg brown oil), of which 60 mg (0.17 mmole) were dissolved in 2-butanone (1.5 ml), and subsequently chlorotrimethylsilane (0.33 ml, 2.6 mmole) was added, the mixture stirred from 30 min and evaporated to dryness. The residue was covered with ether (2 ml), mechanically separated from the flask wall, suction filtered and dried under vacuum. The hydrochloride of a polar diastereoisomer of {4-[3-(1H-indol-3-yl)-propenyl]-1-phenylcyclohexyl}dimethylamine was thus obtained as a light brown solid (65 mg, mp. 118 to 122° C.).

Example 9

{4-[3-(1H-indol-3-yl)-propenyl]-1-phenylcyclohexyl}dimethylamine hydrochloride, less polar diastereoisomer As described for Example 8, less polar diastereoisomers of {4-[3-(1H-indol-3-yl)-propenyl]-1-phenylcyclohexyl}dimethylamine were not obtained cleanly. For purification, 750 mg non-polar crude product were suspended in 95 ml water and 1 ml 85% by weight phosphoric acid. The suspension was shaken with diethyl ether (3×20 ml), the diethyl ether was decanted off in each case and the solid subsequently suction filtered and washed with diethyl ether (10×3 ml). The solid was dried, dissolved in DMF and 1M NaOH (10 ml) added. The alkaline solution was extracted with EE (5×10 ml). The combined EE phases were dried, filtered and evaporated. The residue obtained, 309 mg of a less polar diastereoisomer of {4-[3-(1H-indol-3-yl)-propenyl]-1-phenylcyclohexyl}dimethylamine (viscous oil), was dissolved in 2-butanone (5 ml), and subsequently chlorotrimethylsilane (0.33 ml, 2.6 mmole) was added and the mixture stirred overnight at RT. After adding diethyl ether (3 ml) and a further 30 min, the precipitated hydrochloride of a less polar diastereoisomer of 4-[3-(1H-indol-3-yl)-propenyl]-1-phenylcyclohexyl}dimethylamine was suction filtered and isolated in a yield of 137 mg (beige solid, mp. 138 to 142° C.).

Example 10

3-[3-tert-butoxycarbonyloxy-3-(4-dimethylamino-4-phenylcyclohexyl)-prop-1-ynyl]indole-1-carboxylic acid-tert-butylester, less polar diastereoisomer

AND

Example 11

3-[3-tert-butoxycarbonyloxy-3-(4-dimethylamino-4-phenylcyclohexyl)-prop-1-ynyl]indole-1-carboxylic acid-tert-butyl ester, polar diastereoisomer

AND

Example 12

3-[3-(4-dimethylamino-4-phenyl-cyclohexyl)-3-hydroxyprop-1-ynyl]-indole-1-carboxylic acid-tert-butyl ester Di-tert-butyldicarbonate (18.0 g, 82.6 mole) and 4-dimethylamino pyridine (5 mg) were added at RT and while stirring to a solution of 1H-indole-3-carbaldehyde (10 g, 68.8 mmole) in abs. THF (150 ml) and stirred for 15 min at RT. For working up, the solvent volume was halved, and saturated ammonium chloride solution (100 ml) and ether (160 ml) were added. The aqueous phase was shaken out with ether (3×50 ml) and the combined organic phases were washed with water (2×50 ml) and saturated sodium chloride solution (1×50 ml), dried, filtered and evaporated. 15.4 g 3-formyl-indole-1-carboxylic acid-tert-butylester were obtained as a yellow solid (mp. 124 to 126° C.).

Triphenylphosphane (17.2 g, 65.5 mmole) was added in portions at 0° C., while stirring and within 60 min to a solution of tetrabromocarbon (10.9 g, 32.7 mmole) in DCM (120 ml) and post-stirred for 1 h at 0° C. 3-formyl-indole-1-carboxylic acid-tert-butylester (4 g, 16.4 mmole) dissolved in DCM (30 ml) was subsequently added dropwise within 30 min and the mixture stirred for 4 h at 0° C. After heating the solution to RT, hexane (300 ml) was added and the mixture stirred for 30 min at RT. The mixture was suction filtered and post-washed with hexane. The filtrate was evaporated, a yellow solid being obtained. Chromatographic purification on silica gel was carried out using cyclohexane/EE (95:5). 6.26 g 3-(2,2-dibromovinyl)-indole-1-carboxylic acid-tert-butylester were obtained (white solid, mp. 101 to 104° C.). A solution of 3-(2-2,-dibromovinyl)-indole-1-carboxylic acid-tert-butylester (2.97 g, 7.4 mmole) in THF (20 ml) was introduced at −78° C. under argon, and subsequently a 1.6 M solution of n-butyllithium in hexane (5.7 ml, 9.1 mmole) was added within 30 min, the mixture stirred for 1 h at −78° C., brought to room temperature and then added to a solution, cooled to −78° C., of 4-dimethylamino-4-phenylcycohexane carbaldehyde (580 mg, 2.5 mmole) in THF (10 ml). The mixture was stirred for 8 h at −78° C., brought to room temperature and water (20 ml) was added. For working up, the aqueous phase was extracted with toluene (3×15 ml). The combined organic phase was washed with saturated $NH_4Cl$, 0.2M NaOH and water (about 20 ml in each case), dried over sodium sulfate, filtered and evaporated. First chromatographic purification of the substance mixture obtained was carried out using acetonitrile/methanol/1M $NH_4Cl$ (9:1:1) on silica gel. Three compounds were obtained following a second column chromatographic separation with methanol on silica gel:

90 mg of the less polar diastereoisomer of 3-[3-tert-butoxycarbonyloxy-3-(4-dimethylamino-4-phenylcyclohexyl)-prop-1-ynyl]indole-1-carboxylic acid-tert-butylester (mp. 111 to 117° C.) and 90 mg of the polar diastereoisomer of 3-[3-tert-butoxycarbonyloxy-3-(4-dimethylamino-4-phenylcyclohexyl)-prop-1-ynyl]indole-1-carboxylic acid-tert-butylester (mp. 75 to 79° C.) and 106 mg 3-[3-(4-dimethylamino-4-phenyl-cyclohexyl)-3-hydroxyprop-1-ynyl]-indole-1-carboxylic acid-tert-butylester (mp. above 115° C.).

Efficacy Tests on Compounds According to the Invention:

The data which has been compiled in the following assays and models is summarized in Table 1.

Measurement of ORL1 Binding

The 4-alkyl-/4-alkenyl-/4-alkynylmethyl/-1-aryl-cyclohexylamine compounds corresponding to formula I were examined in a receptor-binding assay with $^3$H-nociceptin/orphanin FQ with membranes of recombinant CHO-ORL1 cells. This test system was implemented by the methods presented by Ardati et al (Mol. Pharmacol., 51, 1997, pp. 816 to 824). The concentration of $^3$H-nociceptin/orphanin FQ was 0.5 nM in these tests. The binding assays were carried out with 20 μg membrane protein per 200 μl batch in 50 mM Hepes, pH 7.4, 10 mM MgCl₂ and 1 mM EDTA. The binding with the ORL1 receptor was determined by using 1 mg WGA-SPA beads (Amersham-Pharmacia, Freiburg), by incubation of the batch for one hour at RT and subsequent measurement in the Trilux scintillation counter (Wallac, Finland). The affinity is shown in Table 1 as a nanomolar $K_i$ value in or % inhibition at c=1 µM.

Measurement of µ-Binding

The receptor affinity for human µ-opiate receptor was determined in a homogeneous batch in microtitre plates. For this purpose, dilution series of the respective 4-alkyl-/4-alkenyl-/4-alkynylmethyl/-1-aryl-cyclohexylamine compound to be tested were incubated with a receptor membrane preparation (15 to 40 µg protein per 250 µl incubation batch) of CHO-K1 cells, which express the human µ-opiate receptor (RB-HOM receptor membrane preparation from NEN, Zaventem, Belgium) in the presence of 1 nmol/l of the radioactive ligand [³H]-naloxone (NET719, NEN, Zaventem, Belgium) and 1 mg WGA-SPA beads (wheat germ agglutinin SPA beads from Amersham/Pharmacia, Freiburg, Germany) in a total volume of 250 µl for 90 minutes at room temperature. 50 mmol/l tris-HCl were added as an incubation buffer with 0.05% by weight sodium azide and 0.06% by weight bovine serum albumin. 25 µmol/l naloxone were also added to determine the non-specific binding. At the end of the 90-minute incubation period, the microtitre plates were centrifuged off for 20 minutes at 1,000 g and the radioactivity measured in a β-counter (Microbeta-Trilux, PerkinElmer Wallac, Freiburg, Germany). The percentage displacement of the radioactive ligand from its binding with the human µ-opiate receptor at a concentration of the test substances of 1 µmol/l was determined and given as a percentage inhibition (% inhibition) of the specific binding. $IC_{50}$ inhibition concentrations, which bring about a 50% displacement of the radioactive ligand, were partially calculated by taking as a basis the percentage displacement by various concentrations of the compounds corresponding to formula I to be tested. Ki values for the test substances were obtained as a result of conversion by means of the Cheng-Prusoff equation.

Testing of Analgesia by Writhing in Mice

The test for analgesic efficacy was carried out using phenylquinone-induced writhing on mice (modified according to I. C. Hendershot and J. Forsaith (1959) J. Pharmacol. Exp. Ther. 125, 237 to 240). For this purpose, male NMRI mice weighing 25 to 30 g were used. 10 minutes after intravenous administration of the test substances, groups of 10 animals per substance dose intraperitoneally received 0.3 ml/mouse of a 0.02% aqueous solution of phenylquinone (phenylbenzoquinone, Sigma, Deisenhofen; preparation of the solution by adding 5% ethanol and storage in a water bath at 45° C.). The animals were placed on their own in observation cages. The number of pain-induced stretching movements (referred to as writhing reactions, i.e. flattening of the body with stretching of the rear extremities) were counted using a push-button counter 5 to 20 minutes after administration of the phenylquinone. Animals which received only physiological saline solution were used as the control. All substances were tested in the standard dose of 10 mg/kg. The percentage inhibition (% inhibition) of the writhing reaction by a substance was calculated according to the following formula:

$$\% \text{ inhibition} = 100 - \frac{\text{writhing reactions of treated animals} * 10}{\text{writhing reactions of control animals}}$$

For some substances the $ED_{50}$ value was calculated, by means of regression analysis (evaluation programme Martens EDV Service, Eckental), from the dose-dependent decrease in the writhing reactions compared with simultaneously investigated phenylquinone control groups, with a 95% confidence interval.

TABLE 1

| Example no. | ORL1 Ki[nM] or % inhibition [1 µM] | µ Ki[nM] or % inhibition [1 µM] | Writhing (mouse, i.v.) ED₅₀ [mg/kg] or % inhibition (dose [mg/kg]) |
|---|---|---|---|
| 1 | 210 | 200 | |
| 2 | 530 | 78 | |
| 3 | 200 | 42 | 100 (10) |
| 4 | 42 | 6.9 | |
| 5 | 140 | 140 | |
| 6 | 340 | 86 | |
| 7 | 89 | 140 | |
| 8 | 55 | 79 | |
| 9 | 110 | 25 | 89 (10) |
| 10 | | 310 | |
| 11 | | 55% | |
| 12 | 730 | 88 | |

Parenteral solution of 4-alkyl-/4-alkenyl-/4-alkynylmethyl/-1-aryl-cyclohexylamine compound according to the invention 38 g of one of the 4-alkyl-/4-alkenyl-/4-alkynylmethyl/-1-aryl-cyclohexylamine compounds according to the invention, in this case Example 1, were dissolved at room temperature in 1 liter of water for injection purposes and subsequently adjusted to isotonic conditions for injection purposes by adding anhydrous glucose.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A 4-alkyl-/4-alkenyl-/4-alkynyl methyl/-1-aryl-cyclohexylamine compound corresponding to formula I

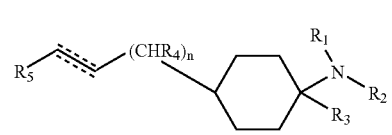

wherein
the line illustrated thus:

represents a single, double or triple bond;
R¹ and R² independently represent H; respectively saturated or unsaturated, branched or unbranched, singly or multiply substituted or unsubstituted $C_{1-8}$ alkyl or $C_{3-8}$ cycloalkyl; respectively singly or multiply substituted or unsubstituted aryl or heteroaryl; or respectively singly or multiply substituted or unsubstituted aryl, $C_{3-8}$ cycloalkyl or heteroaryl connected via $C_{1-3}$ alkyl, or $R^1$ and $R^2$ together form a ring and represent $CH_2CH_2OCH_2CH_2$, $CH_2CH_2NR^6CH_2CH_2$ or $(CH_2)_{3-6}$, wherein $R^6$ represents H; respectively saturated or unsaturated, branched or unbranched, singly or multiply substituted or unsubstituted $C_{1-8}$ alkyl or $C_{3-8}$ cycloalkyl; respectively singly or multiply substituted or unsubstituted aryl or heteroaryl; or respectively singly or multiply substituted or unsubstituted aryl, $C_{3-8}$ cycloalkyl or heteroaryl bound by $C_{1-3}$ alkyl;

$R^3$ represents respectively saturated or unsaturated, branched or unbranched, singly or multiply substituted or unsubstituted $C_{1-8}$ alkyl or $C_{3-8}$ cycloalkyl; respectively unsubstituted or singly or multiply substituted aryl or heteroaryl; respectively unsubstituted or singly or multiply substituted aryl, $C_{3-8}$ cycloalkyl or heteroaryl bound by a saturated or unsaturated, branched or unbranched or substituted or unsubstituted $C_{1-4}$ alkyl group;

$R^4$ represents H, OH or an O protecting group, wherein n=0 or 1; and $R^5$ represents respectively unsubstituted or singly or multiply substituted $C_{3-8}$ cycloalkyl, aryl or heteroaryl; —$CH_2R^{12}$, —$CH_2$—$CH_2R^{12}$, or —$CH_2$—$CH_2$—$CH_2R^{12}$, wherein $R^{12}$ represents respectively unsubstituted or singly or multiply substituted $C_{3-8}$ cycloalkyl, aryl or heteroaryl, or a physiologically acceptable salt or solvate thereof.

2. A compound according to claim 1, wherein said compound is present in the form of a racemate.

3. A compound according to claim 1, wherein said compound is present in the form of a pure stereoisomer or a pure enantiomer or diastereomer.

4. A compound according to claim 1, wherein said compound is present in the form of a mixture of stereoisomers.

5. A 4-alkyl-/4-alkenyl-/4-alkynylmethyl/-1-aryl-cyclohexylamine compound according to claim 1, wherein $R^1$ and $R^2$ independently represent H; or saturated or unsaturated, branched or unbranched, singly or multiply substituted or unsubstituted $C_{1-8}$ alkyl; or $R^1$ and $R^2$ together form a ring and represent $CH_2CH_2OCH_2CH_2$, $CH_2CH_2NR^6CH_2CH_2$ or $(CH_2)_{3-6}$, wherein $R^6$ represents H; or saturated or unsaturated, branched or unbranched, singly or multiply substituted or unsubstituted $C_{1-8}$ alkyl.

6. A compound according to claim 5, wherein $R^1$ and $R^2$ independently represent H; or saturated or unsaturated, branched or unbranched, singly or multiply substituted or unsubstituted $C_{1-4}$ alkyl, with the proviso that $R^1$ and $R^2$ are not both H, or $R^1$ and $R^2$ together form a ring and represent $(CH_2)_{4-5}$.

7. A compound according to claim 6, wherein $R^1$ and $R^2$ independently represent methyl or ethyl, or $R^1$ and $R^2$ together form a ring and represent $(CH_2)_5$.

8. A 4-alkyl-/4-alkenyl-/4-alkynylmethyl/-1-aryl-cyclohexylamine compound according to claim 1, wherein $R^1$ and $R^2$ independently represent $CH_3$ or H, with the proviso that $R^1$ and $R^2$ are not both H.

9. A 4-alkyl-/4-alkenyl-/4-alkynylmethyl/-1-aryl-cyclohexylamine compound according to claim 1, wherein $R^3$ represents unsubstituted or singly or multiply substituted $C_{3-8}$ cycloalkyl, aryl or heteroaryl; or respectively unsubstituted or singly or multiply substituted aryl, $C_{3-8}$ cycloalkyl or heteroaryl connected via a saturated or unsaturated, unbranched, substituted or unsubstituted $C_{1-2}$ alkyl group.

10. A compound according to claim 9, wherein $R^3$ represents respectively unsubstituted or singly or multiply substituted cyclopentyl, cyclohexyl, phenyl, benzyl, naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl; or respectively unsubstituted or singly or multiply substituted $C_{5-6}$ cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl connected via a saturated, unbranched $C_{1-2}$ alkyl group.

11. A compound according to claim 10, wherein $R^3$ represents respectively unsubstituted or singly or multiply substituted phenyl, furyl, thiophenyl, naphthyl, benzyl, benzofuranyl, indolyl, indanyl, benzodioxanyl, benzodioxolanyl, pyridyl, pyrimidyl, pyrazinyl or benzothiophenyl; or respectively unsubstituted or singly or multiply substituted phenyl, furyl or thiophenyl connected via a saturated, unbranched $C_{1-2}$ alkyl group.

12. A 4-alkyl-/4-alkenyl-/4-alkynylmethyl/-1-aryl-cyclohexylamine compound according to claim 1, wherein $R^3$ represents respectively substituted or unsubstituted phenyl, thiophenyl, pyridyl or benzyl.

13. A 4-alkyl-/4-alkenyl-/4-alkynylmethyl/-1-aryl-cyclohexylamine compound according to claim 1, wherein $R^4$ represents H, OH, benzyloxycarbonyloxy, acetyloxy or OBoc.

14. A 4-alkyl-/4-alkenyl-/4-alkynylmethyl/-1-aryl-cyclohexylamine compound according to claim 1, wherein $R^5$ represents respectively unsubstituted or singly or multiply substituted $C_{3-8}$ cycloalkyl, aryl or heteroaryl.

15. A compound according to claim 14, wherein $R^5$ represents respectively unsubstituted or singly or multiply substituted cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl, pyrimidyl, fluorenyl, fluoranthenyl, benzothiazolyl, benzotriazolyl, benzo[1,2,5]thiazolyl, 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl.

16. A compound according to claim 15, wherein $R^5$ represents respectively unsubstituted or singly or multiply substituted cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl.

17. A 4-alkyl-/4-alkenyl-/4-alkynylmethyl/-1-aryl-cyclohexylamine compound according to claim 1, wherein $R^5$ represents —$CH_2R^{12}$, —$CH_2$—$CH_2R^{12}$, or —$CH_2$—$CH_2$—$CH_2R^{12}$.

18. A compound according to claim 17, wherein $R^5$ represents —$CH_2R^{12}$, or —$CH_2$—$CH_2R^{12}$.

19. A compound according to claim 18, wherein $R^5$ represents —$CH_2R^{12}$, wherein $R^{12}$ represents respectively unsubstituted or singly or multiply substituted $C_{3-8}$ cycloalkyl, aryl or heteroaryl.

20. A 4-alkyl-/4-alkenyl-/4-alkynylmethyl/-1-aryl-cyclohexylamine compound according to claim 17, wherein $R^{12}$ represents respectively unsubstituted or singly or multiply substituted cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl, pyrimidyl, fluorenyl, fluoranthenyl, benzothiazolyl, benzotriazolyl, benzo[1,2,5]thiazolyl, 1,2-dihydroacenaphthenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl.

21. A compound according to claim 20, wherein $R^{12}$ represents respectively unsubstituted or singly or multiply substituted cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl.

22. A 4-alkyl-/4-alkenyl-/4-alkynylmethyl/-1-aryl-cyclohexylamine compound according to claim 1, selected from the group consisting of dimethyl-[1-phenyl-4-(2-p-tolylvinyl)cyclohexyl]amine hydrochloride, most polar diastereoisomer;

dimethyl-[1-phenyl-4-(2-p-tolylvinyl)cyclohexyl]amine hydrochloride, second most polar diastereoisomer;

dimethyl-[1-phenyl-4-(2-p-tolylvinyl)cyclohexyl]amine hydrochloride, least polar diastereoisomer;

{4-[2-(4-fluorophenyl)vinyl]-1-phenylcyclohexyl}dimethylamine hydrochloride, least polar diastereoisomer;

{4-[2-(4-fluorophenyl)vinyl]-1-phenylcyclohexyl}dimethylamine hydrochloride, second least polar diastereoisomer;

{4-[2-(4-fluorophenyl)vinyl]-1-phenylcyclohexyl}dimethylamine hydrochloride, second most polar diastereoisomer;

{4-[2-(4-fluorophenyl)vinyl]-1-phenylcyclohexyl}dimethylamine hydrochloride, most polar diastereoisomer;

{4-[3-(1H-indol-3-yl)-propenyl]-1-phenylcyclohexyl}dimethylamine hydrochloride, more polar diastereoisomer;

{4-[3-(1H-indol-3-yl)-propenyl]-1-phenylcyclohexyl}dimethylamine hydrochloride, less polar diastereoisomer;

3-[3-tert-butoxycarbonyloxy-3-(4-dimethylamino-4-phenylcyclohexyl)-prop-1-ynyl]-indole-1-carboxylic acid-tert-butylester, less polar diastereoisomer;

3-[3-tert-butoxycarbonyloxy-3-(4-dimethylamino-4-phenylcyclohexyl)-prop-1-ynyl]-indole-1-carboxylic acid-tert-butylester, more polar diastereoisomer;

3-[3-(4-dimethylamino4-phenyl-cyclohexyl)-3-hydroxyprop-1-ynyl]-indole-1-carboxylic acid-tert-butylester; and mixtures of at least two of the foregoing.

23. A pharmaceutical composition comprising as an active ingredient at least one 4-alkyl-/4-alkenyl-/4-alkynylmethyl/-1-aryl-cyclohexylamine compound according to claim 1, and at least one pharmaceutically acceptable additive or auxiliary or additional active ingredient.

24. A method of treating or inhibiting pain in a patient in need thereof, said method comprising administering to said patient an effective amount of a compound according to claim 1.

25. A method according to claim 24, wherein said pain is selected from the group consisting of acute pain, visceral pain, neuropathic pain and chronic pain.

26. A method of producing a 4-alkyl-/4-alkenyl-/4-alkynylmethyl/-1-aryl-cyclohexylamine compounds according to claim 1, said method comprising reacting a 4-aminocyclohexane carbaldehyde compound with a Wittig reagent corresponding to formula $R^5CH_2PPh_3X$ in the presence of base to obtain an olefin, and hydrogenating the olefin.

27. A method according to claim 26, wherein the olefin is hydrogenated catalytically with $H_2$ using Pd/C.

28. A method for producing a 4-alkyl-/4-alkenyl-/4-alkynylmethyl/-1-aryl-cyclohexylamine compound according to claim 1, said method comprising:

reacting a 4-aminocyclohexanone with an organometallic compound produced from $R^5CH_2CH_2Br$ or $R^5CH_2CH_2Cl$ with the addition of magnesium or n-BuLi to obtain an addition product, and subsequently dehydrating the addition product with treatment with an acid to obtain an olefin, and catalytically hydrogenating the olefin with $H_2$ using Pd/C as catalyst.

29. A method for producing a 4-alkyl-/4-alkenyl-/4-alkynylmethyl/-1-aryl-cyclohexylamine compound according to claim 1, said method comprising: reacting a 4-aminocyclohexyl carbaldehyde with

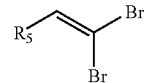

in the presence of n-BuLi to form a 4-alkynylmethyl-cyclohexylamine compound, wherein $R^4$ represents OH.

30. A method according to claim 29, wherein the OH function is provided with a protecting group, and the triple bond is subsequently hydrogenated using $H_2$/Pd or $H_2$/Lindlar catalyst.

31. A method for producing a 4-aminocyclohexane carbaldehyde compound according to claim 1, said method comprising reacting a 4-aminocyclohexanone compound with methoxytriphosphonium chloride and a base, and subsequently with aqueous acid.

* * * * *